US005122542A

United States Patent [19]
Mao et al.

[11] Patent Number: 5,122,542
[45] Date of Patent: Jun. 16, 1992

[54] HYPOTRIGLYCERIDEMIC USE OF CERTAIN BIS (3,5-DI-ALKYL-4-HYDROXYPHENYLTHIO)METHANES

[75] Inventors: Simon J. T. Mao, Loveland; George Ku, West Chester; Richard L. Jackson, Cincinnati, all of Ohio

[73] Assignee: Merrell Dow Pharmaceuticals Inc., Cincinnati, Ohio

[21] Appl. No.: 540,657

[22] Filed: Jun. 19, 1990

[51] Int. Cl.$^5$ ............................................. A61K 31/10
[52] U.S. Cl. ..................................................... 514/712
[58] Field of Search ......................................... 514/712

[56] References Cited

U.S. PATENT DOCUMENTS

| | | | |
|---|---|---|---|
| 4,734,527 | 3/1988 | Krauss | 568/47 |
| 4,900,757 | 2/1990 | Mao et al. | 514/712 |
| 4,954,528 | 9/1990 | Mao et al. | 514/712 |
| 4,959,392 | 9/1990 | Robinson et al. | 514/712 |

OTHER PUBLICATIONS

Patton, James G., *Clin. Chem.* 29: 1890, pp. 1890–1897 (1983).
Vega, Gloria Lena and Grundy, Scott M., *Adv. Ex. Med. Biol.* 243: 311–326, (1989).
Soergel, Konrad H., *Gastrointestinal Disease*, 3rd Edition, Chapter 91:1462–85 (1983).
Brown, Michael S., et al., *The Pharmacological Basis of Therapeutics*, 7th Edition, Chapter 34:827–845 (1985).

*Primary Examiner*—Frederick E. Waddell
*Assistant Examiner*—Kimberly R. Jordan
*Attorney, Agent, or Firm*—Louis J. Wille

[57] ABSTRACT

The present invention relates to a method of lowering plasma triglycerides in a patient in need thereof comprising administering to said patient an effective hypotriglyceridemic amount of a bis(3,5-di-alkyl-4-hydroxyphenylthio)methane.

3 Claims, No Drawings

HYPOTRIGLYCERIDEMIC USE OF CERTAIN BIS (3,5-DI-ALKYL-4-HYDROXYPHENYLTHIO)METHANES

BACKGROUND OF THE INVENTION

Hypertriglyceridemia is a disease state in which there is an excessive amount of triglyceride in the plasma. Hypertriglyceridemia can lead to various undesirable effects. For example, hypertriglyceridemia can cause increases in concentrations of certain abnormal lipoproteins which may play a role in atherogenesis and the development of coronary heart disease. In addition, hypertriglyceridemia is known to be a cause of acute pancreatitis which can be a life-threatening condition. It is therefore desirable to provide a method for reducing plasma triglycerides in patients with hypertriglyceridemia.

Triglycerides in the diet are hydrolyzed in the intestine to monoglycerides and fatty acids. These hydrolysis products are absorbed by the intestinal mucosa where they are resynthesized into triglycerides. These triglycerides are then incorporated into lipoproteins called chylomicrons which contain cholesterol, phospholipid and triglycerides in addition to a protein component. The triglyceride-rich chylomicrons are secreted into the blood stream via the lymph system. Circulating chylomicrons are exposed to the enzyme lipoprotein lipase which catalyzes the hydrolysis of chylomicron triglycerides to free fatty acids. After the removal of most of the triglycerides, the chylomicron remnant, which is now cholesterol-rich, is further removed from the blood stream by the liver.

In addition, the liver secretes into the blood stream endogenous triglyceride-rich lipoproteins called very low density lipoproteins (VLDL). As the VLDL circulates, a portion of the VLDL-associated triglycerides is removed by lipolysis catalyzed by lipoprotein lipase and hepatic triglyceride lipase. At the same time, the circulating VLDL pick up cholesterol ester from other circulating lipoproteins such as high density lipoproteins (HDL). Circulating VLDL continue to undergo these modifications leading to progressively smaller particles which are depleted in triglycerides and enriched in cholesterol ester. The triglyceride-depleted VLDL are cleared by the liver or are degraded further to another form of lipoprotein called low density lipoprotein (LDL). Although LDL normally carry relatively small amounts of triglycerides and do not play a major role in triglyceride transport in the blood, various epidemiologic studies have indicated that LDL cholesterol levels correlate well with the risk of coronary heart disease [Patton et al., Clin. Chem. 29, 1890 (1983)]. It is generally accepted by those skilled in the art that reduction of abnormally high LDL cholesterol levels is effective therapy in the treatment of atherosclerosis.

The presence of hypertriglyceridemia in a patient can cause abnormalities in all of the circulating lipoproteins. Endogenous hypertriglyceridemia causes prolonged chylomicronemia and increases in partially catabolized chylomicron remnants following fat ingestion. Hypertriglyceridemia is also associated with a prolonged residence time of VLDL in the circulation and gives rise to several changes in VLDL composition. These modified VLDL are more readily taken up by macrophages to form fatty foam cells which eventually lead to the formation of atherosclerosis. Various compositional changes in LDL and HDL also occur as a result of hypertriglyceridemia leading to abnormal LDL and HDL.

Although the presence of hypertriglyceridemia may not be atherogenic per se, since triglycerides do not themselves accumulate in atherosclerotic plaque and elevated plasma triglyceride does not appear to be an independent risk factor for coronary heart disease in epidemiologic studies, hypertriglyceridemia can lead to the formation of certain abnormal circulating lipoproteins which may themselves be atherogenic [See Vega and Grundy, Adv. Exp. Med. Biol. 243, 311 (1989)]. Reduction of triglyceride levels in a patient suffering from hypertriglyceridemia can therefore provide the beneficial effect of reducing levels of certain abnormal atherogenic lipoproteins.

Acute pancreatitis is a process of autodigestion caused by the premature activation of zymogens to the corresponding active digestive enzymes within the pancreas. It is well accepted that elevated circulating triglyceride levels can trigger attacks of acute pancreatitis. It is further well accepted that recurrences of attacks of acute pancreatitis can be prevented by treatment aimed at lowering plasma triglyceride levels [See K. Soergel, ACUTE PANCREATITIS, in Gastrointestinal Disease 91, 3rd ed. (Sleisenger, M. H., and Fordtran, J. S., eds.), W. B. Saunders Company, Philadelphia, Pa., 1983, pp. 1462-1485; and See Brown, M. S., and Goldstein, J. L., DRUGS USED IN THE TREATMENT OF HYPERLIPOPROTEINEMIAS, in Goodman and Gillman's, The Pharmacological Basis of Therapeutics 34, 7th edition, (Macmillan Publishing Co., New York, 1985, pp. 827-845].

The present invention relates to the use of certain bis(3,5-di-alkyl-4-hydroxyphenylthio)methanes, such as bis(3,5-di-tertiarybutyl-4-hydroxyphenylthio)methane, in treating patients suffering from hypertriglyceridemia. Bis(3,5-di-tertiarybutyl-4-hydroxyphenylthio)methane is disclosed in U.S. Pat. No. 4,900,757 as providing a hypocholesterolemic and a antiatheroscleotic effect in patients treated therewith.

SUMMARY OF THE INVENTION

The present invention provides a method of lowering plasma triglycerides in a patient in need thereof comprising administering to said patient an effective hypotriglyceridemic amount of a compound of formula (1)

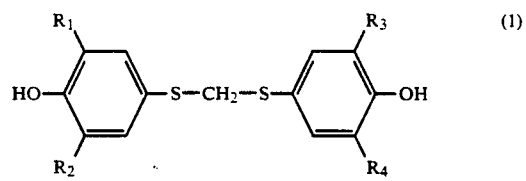

wherein $R_1$, $R_2$, $R_3$ and $R_4$ are each independently a $C_1$-$C_6$ alkyl group.

The present invention further provides a method of treating a patient suffering from hypertriglyceridemia comprising administering to said patient an effective hypotriglyceridemic amount of a compound of formula (1).

DETAILED DESCRIPTION OF THE INVENTION

As used herein, the term "$C_1$-$C_6$ alkyl group" means and includes saturated alkyl groups of straight, cyclic or branched-chain configuration made up of from one to six carbon atoms. Included within the scope of this term are methyl, ethyl, n-propyl, isopropyl, n-butyl, isobutyl, secbutyl, tertiarybutyl and the like. The compound of formula (1) wherein $R_1$, $R_2$, $R_3$ and $R_4$ are each tertiarybutyl, or bis(3,5-di-tertiary-butyl-4-hydroxyphenylthio)methane, is preferred in the method of use according to the present invention.

As used herein, the term "patient" refers to warm-blooded animals or mammals, including rodents and humans, who are in need of treatment for hypertriglyceridemia. Patients are in need of treatment for hypertriglyceridemia, for example, in the case of a patient suffering from Type IV Hyperlipoproteinemia (indicating elevated VLDL) according to the Fredrickson classification [Fredrickson and Levy, FAMILIAL HYPERLIPOPROTEINEMIA, in The Metabolic Basis of Inherited Disease, 3rd ed. (Stanbury, J. B.; Wyngaarden, J. B.; and Fredrickson, D. S.; eds.) McGraw-Hill Book Co., New York, 1972, pp. 545–614].

Hypertriglyceridemia is a disease state characterized by levels of plasma triglycerides which are elevated by a clinically significant amount over that considered normal by those of ordinary skill in the art. The identification of those patients who are in need of treatment for hypertriglyceridemia is well within the ability and knowledge of one skilled in the art. For example, individuals who have plasma triglyceride levels, as determined by clinical laboratory tests, which are substantially and chronically elevated over that considered normal by those of ordinary skill in the art, are patients in need of treatment for hypertriglyceridemia. By way of further example, individuals who are at risk of developing hypertriglyceridemia can also represent patients in need of treatment for hypertriglyceridemia. A clinician skilled in the art can readily identify, by the use of clinical tests, physical examination and medical/family history, those patients who are suffering from hypertriglyceridemia and those who are at risk of developing hypertriglyceridemia and thus readily determine if an individual is a patient in need of treatment for hypertriglyceridemia.

An effective hypotriglyceridemic amount of a compound of formula (1) is an amount which is effective in reducing plasma triglyceride levels in a patient in need thereof. As such, successful treatment of a patient for hypertriglyceridemia is understood to include reducing a patient's plasma triglyceride levels. Successful treatment for hypertriglyceridemia is also understood to include prophylaxis in preventing clinically significant elevations in plasma triglyceride levels in a patient who is at risk of the development of hypertriglyceridemia.

An effective hypotriglyceridemic dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective hypotriglyceridemic amount of a compound of formula (1) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, a compound formula (1) may be incorporated with excipients and used in the form of tablets, troches, capsules, elixirs, suspensions, syrups, wafers, chewing gums and the like. These preparations should contain at least 4% of the compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The compounds of formula (1) can be prepared by methods well known and appreciated by those of ordinary skill in the art. For example, a compound of formula (1) can be prepared by treating the appropriate 2,6-di-alkyl-4-mercaptophenol with 1,3,5-trioxane in the presence of acetonitrile and DOWEX 50 resin under reflux conditions. 2,6-Di-alkyl-4-mercaptophenols can be prepared as described, for example, by Krauss in U.S. Pat. No. 4,734,527, which discloses the preparation of 2,6-di-tertiarybutyl-4-mercaptophenol.

In the end use application provided by the present invention, the preferred compound of formula (1) is bis(3,5-di-tertiarybutyl-4-hydroxyphenylthio)methane. The following examples illustrate the preparation and use of bis(3,5-di-tertiarybutyl-4-hydroxyphenylthio)methane according to the present invention. These examples are illustrative only and are not intended to limit the scope of the invention in any way.

EXAMPLE 1

Preparation of Bis(3,5-di-tertiarybutyl-4-hydroxyphenylthio)methane

Combine acetonitrile [1800 milliliters (ml)], 1,3,5-trioxane [71.0 grams (gm), 0.79 moles (mol)], 2,6-di-tertiarybutyl-4-mercaptophenol [678.4 gm, 2.85 mol] and 2.5 gm DOWEX 50 resin in a three-necked flask with a thermowell. Bring the mixture to reflux under a nitrogen atmosphere and maintain for 36–48 hours to provide the title compound.

Filter the mixture to remove the DOWEX 50 resin and concentrate the filtrate in vacuo to give an amber oil. Dissolve the oil in 1 liter of ethanol at 70 degrees Celsius (°C.) and add 125 ml of water. Allow the mixture to cool to ambient temperature over night while stirring. Collect the resulting crystalline product by filtration and wash the filter cake with 75 ml of cold ethanol/water (90/10). Recrystallize the product from ethanol/water and collect by filtration. Wash the filter cake with 50 ml of cold ethanol and dry the product in a vacuum oven at 50° C. and 15 mm Hg overnight to yield 406.9 gm of the purified title compound as a white solid. Melting point 94°–95° C. Elemental analysis:
Calculated—C=71.3%, H=9.07%;
Found—C=71.3%, H=9.09%.

EXAMPLE 2

Hypotriglyceridemic Effect of Bis(3,5-di-tertiarybutyl-4-hydroxyphenylthio)methane Mice were separated into 2 Treatment Groups of 4 or 5 animals per group and were treated for 21 days as follows:
Group 1 (Control, 4 animals)—animals were fed standard rodent chow;
Group 2 (Treated, 5 animals)—animals were fed standard rodent chow containing 0.25% bis(3,5-di-tertiarybutyl-4-hydroxyphenylthio)methane.

After 21 days, the animals were sacrificed and blood samples were taken. Plasma triglyceride was determined by a standard enzymatic method using a DACOS analyzer (Coulter Electronics, Inc., Hialeah, Fla., USA).

The results of treatment of mice with bis(3,5-di-tertiary-butyl-4-hydroxyphenylthio)methane is shown in Table 1.

TABLE 1

| Effect of Bis(3,5-di-tertiary-butyl-4-hydroxyphenylthio)methane in the Mouse | |
|---|---|
| Treatment Group | Plasma Triglycerides (mg/dL ± S.D.) |
| 1. Control | 273 ± 80 |
| 2. Compound A | 87 ± 20* |

Compound A = bis(3,5-di-tertiarybutyl-4-hydroxyphenylthio)methane
*p < 0.001

These results indicate that administration of bis(3,5-di-tertiarybutyl-4-hydroxyphenylthio)methane to mice results in a statistically significant reduction in plasma triglyceride levels.

What is claimed is:

1. A method of lowering plasma triglycerides in a patient in need thereof comprising administering to said patient an effective hypotriglyceridemic amount of a compound of the formula

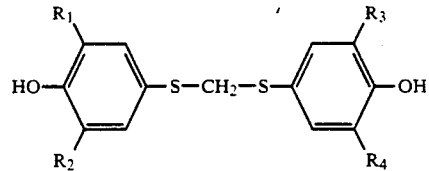

wherein $R_1$, $R_2$, $R_3$ and $R_4$ are each independently a $C_1$–$C_6$ alkyl group.

2. A method of treating a patient suffering from hypertriglyceridemia comprising administering to said patient an effective hypotriglyceridemic amount of a compound of the formula

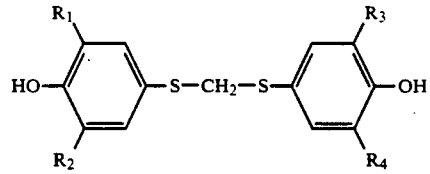

wherein $R_1$, $R_2$, $R_3$ and $R_4$ are each independently a $C_1$–$C_6$ alkyl group.

3. A method according to claim 1 or 2 wherein the compound is bis(3,5-di-tertiarybutyl-4-hydroxyphenylthio) methane.